United States Patent [19]

Teach

[11] 3,937,729
[45] Feb. 10, 1976

[54] META-BIS ANILIDE DERIVATIVES AND THEIR UTILITY AS HERBICIDES

[75] Inventor: Eugene G. Teach, El Cerrito, Calif.

[73] Assignee: Stauffer Chemical Company, Westport, Conn.

[22] Filed: Mar. 19, 1973

[21] Appl. No.: 342,579

Related U.S. Application Data

[63] Continuation of Ser. No. 180,916, Sept. 15, 1971, abandoned, which is a continuation of Ser. No. 20,104, March 16, 1970, abandoned, which is a continuation-in-part of Ser. No. 741,267, July 1, 1968, abandoned, which is a continuation-in-part of Ser. No. 659,865, Aug. 11, 1967, abandoned.

[52] U.S. Cl. ...... 260/557 R; 260/347.3; 260/551 S; 260/558 P; 260/558 D; 260/559 B; 260/559 R; 260/562 R; 260/562 A; 260/562 B; 71/88; 71/98; 71/118
[51] Int. Cl.² .............. C07C 103/44; C07C 103/64; C07C 103/82
[58] Field of Search..................... 260/557, 558, 562

[56] References Cited
UNITED STATES PATENTS

| | | | |
|---|---|---|---|
| 2,231,611 | 2/1941 | Boeseken et al.................... | 260/562 |
| 2,317,130 | 4/1943 | Coes et al........................... | 260/562 |
| 2,402,792 | 6/1946 | Watson et al....................... | 260/558 |
| 2,647,815 | 8/1953 | Buc et al............................. | 260/562 |
| 3,188,346 | 6/1965 | Kalopissis et al. ................. | 260/562 |
| 3,424,767 | 1/1969 | Burdesk et al..................... | 260/562 |

FOREIGN PATENTS OR APPLICATIONS

| | | | |
|---|---|---|---|
| 936,395 | 12/1955 | Germany ........................... | 260/562 |
| 1,368,619 | 6/1964 | France................................ | 260/562 |

OTHER PUBLICATIONS
Pailer et al., Monat. Chem., Vol. 97, p. 1551, (1966).
Berti et al., Arch Pharm., Vol. 285, pp. 372–375, (1952).

Primary Examiner—Harry I. Moatz
Attorney, Agent, or Firm—Harry A. Pacini

[57] ABSTRACT

Compounds corresponding to the formula:

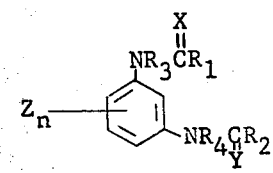

in which $R_1$ and $R_2$ are, independently, hydrogen, alkyl, alkoxyalkyl, cycloalkyl, pinonyl, ethylcycloalkyl, lower alkenyl, halogenated lower alkyl, benzyl, ethylphenyl, 2,4-dichlorophenoxy-methylene, styryl, furyl, phenyl or substituted phenyl in which the substituents are nitro, halogen, methyl, or methoxy; $R_3$ and $R_4$ are, independently, hydrogen or lower alkyl; X and Y are independently oxygen or sulfur; and Z is halogen, nitro, amino, lower alkyl, lower alkoxy or trifluoromethyl and n is an integer having a value from 0 to 4. The above compounds are effective herbicides, particularly for the control of grasses and broadleaf plants with both pre-emergence and post-emergence activity. Representative compounds are: m-propionamidobutyranilide, m-bis-2,2-dimethylvaleranilide, m-isobutyramido trichloroacetanilide, m-isobutyramido-2-ethylbutyranilide, m-t-butylacetamidopropionanilide, and 3'-N-ethyl propionamido-propionalide.

36 Claims, No Drawings

META-BIS ANILIDE DERIVATIVES AND THEIR UTILITY AS HERBICIDES

This application is a continuation of application Ser. No. 180,916, filed Sept. 15, 1971, which is a continuation of application Ser. No. 20,104, filed Mar. 16, 1970, which is a continuation-in-part of application Ser. No. 741,267, filed July 1, 1968, which is a continuation-in-part of application Ser. No. 659,865, filed Aug. 11, 1967, all now abandoned.

This invention relates to herbicidally active meta-bis anilide derivatives. More specifically, this invention relates to certain new compounds and the use as active herbicidal substances of certain substituted meta-bis-anilides.

The novel compounds of the present invention correspond to the general formula:

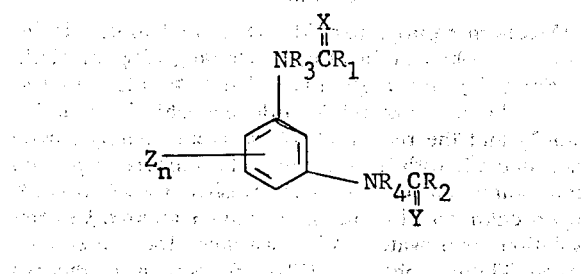

in which $R_1$ and $R_2$ are independently selected from the group consisting of hydrogen, alkyl, alkoxyalkyl, cycloalkyl, pinonoyl, ethylcycloalkyl, lower alkenyl, halogenated lower alkyl, benzyl, furyl, ethylphenyl, 2,4-dichlorophenoxy-methylene, styryl, phenyl, and substituted-phenyl in which said substituents are nitro, halogen, methyl or methoxy; selected from the group consisting of hydrogen and lower alkyl; X and Y are independently oxygen or sulfur; and Z is selected from the group consisting of halogen, nitro, amino, lower alkyl, lower alkoxy, and trifluoromethyl and $n$ is an integer having a value from 0 to 4.

The method of the present invention of controlling undesirable vegetation comprises applying an herbicidally effective amount of the above represented compounds to the area where control is desired. Compounds wherein $R_1$ and $R_2$ are independently selected from the group consisting of alkyl, hydrogen, alkoxyalkyl, cycloalkyl, pinonoyl, ethylcycloalkyl, lower alkenyl, halogenated lower alkyl, benzyl, 2,4-dichlorophenoxymethylene, styryl, phenyl, phenyl and substituted phenyl in which the substituents are nitro, halogen, methyl or methoxy; $R_3$ and $R_4$ are independently selected from the group consisting of hydrogen and lower alkyl; X and Y are independently oxygen or sulfur; and Z is selected from the group consisting of halogen, nitro, amino, lower alkyl, lower alkoxy, and trifluoromethyl and $n$ is an integer having a value from 0 to 4; are within the scope of this aspect of the present invention.

The term alkyl, preferably includes those members of the group which contains from 1 through about 10 carbon atoms, inclusive, in both straight chain and branched chain configurations. The term lower alkyl and lower alkoxy preferably include members of the groups having from 1 through about 6 carbon atoms, inclusive. The term alkoxyalkyl includes members having 2 to 4 carbon atoms. The term cycloalkyl preferably includes members of the group having from 3 through about 6 carbon atoms, inclusive. The term lower alkenyl preferably includes those members of the group containing at least one double bond and containing from 2 to 4 carbon atoms, inclusive.

In its most preferred form, the invention relates to compositions having the formula

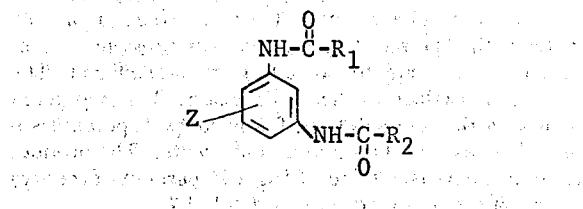

in which $R_1$ and $R_2$ independently are hydrogen, alkyl containing from 1 to 10 carbon atoms, inclusive, alkoxyalkyl containing 2 to 4 carbon atoms, cycloalkyl containing from 3 to 6 carbon atoms, inclusive, pinonoyl, ethylcycloalkyl wherein the cycloalkyl moiety contains from 5 to 6 carbon atoms, inclusive, lower alkenyl containing from 2 to 6 carbon atoms, inclusive, halogenated lower alkyl containing 1 to 6 carbon atoms, inclusive, benzyl, furyl, ethylphenyl, styryl, 2,4-dichlorophenoxy-methylene, phenyl and substituted phenyl in which said substituents are nitro, halogen, especially chlorine and fluorine, methyl, and methoxy; and Z is hydrogen, 4'-chloro, 3'-chloro or 2'-methyl.

The compounds of this invention are prepared by one of several general methods. One such general method is the condensation between the appropriate m-phenylene diamine and an appropriate acid anhydride or chloride to prepare the desired meta-bis-symmetrically substituted anilide. Another general method is the condensation between the appropriate m-mono-substituted amino anilide and an appropriate acide anhydride or acid chloride to prepare the desired meta-bis-assymetrically substituted anilide. The reactions proceed readily in the liquid phase. The employment of a solvent is also useful, facilitating processing, as well as agitation of the reactants. When using a starting material containing an acid chloride, it is preferred to carry out the reaction in the presence of a hydrogen halide acceptor such as triethylamine, pyridine, picoline, sodium carbonate and the like. The reactions are preferably carried out at temperatures that permit operation in the liquid phase.

Compounds of the present invention are prepared in accordance with the following illustrative examples.

EXAMPLE 1

Preparation of Meta-bis-isobutyranilide

Isobutyric anhydride, 26g. (0.16 mole) is added slowly to 8.6g. (0.08 mole) of m-phenylene diamine in an open beaker. The mixture was stirred. The solid product is washed consecutively with water, sodium bicarbonate solution and ether. After drying, there is obtained 18.5g. (92 percent of theory) of the title compound, m.p. 205°–206°C.

The following compounds are typical of those prepared using the method of the foregoing example: m-bis-acetanilide, m-bis-propionanilide, m-bis-n-butyranilide and m-bis-trifluoroacetanilide.

EXAMPLE 2

Preparation of Meta-bis-2,2-dimethyl-valeranilide

Meta-phenylene diamine, 87g. (0.8 moles), is dissolved in one liter of acetone containing 190g. (1.9 moles) of triethylamine. To this solution, 2,2-dimethyl-valeryl chloride, 260g. (1.75 moles) is added slowly with stirring. The reaction flask is cooled in a cold water bath. The resulting mixture is poured into 1-liter of cold water and the resulting oil crystallized. The product is further washed with water, then 5 percent hydrochloric acid solution, followed by 5 percent sodium hydroxide solution and finally water. The product is dried. There is obtained 256g. (96 percent of theory) of the title compound, m.p. 109°–111°C.

The following compounds are typical of those prepared using the method of the foregoing example: m-bis-pivalanilide, m-bis-3,3-dimethylbutyranilide, m-bis-crotonanilide, m-bis-hexanilide, and m-bis-isovalerylanilide.

EXAMPLE 3

Preparation of Meta-propionamido isobutyranilide

Meta-amino propionanilide, 11.5g. (0.07 moles) is treated with isobutyric anhydride, 11.1g. (0.07 moles) is an open beaker. The product is poured into water and washed with 5 percent hydrochloric acid solution, 5 percent sodium hydroxide solution, and water. The product is dried of water. There is obtained 15.2g. (93 percent of theory) of the title compound, m.p. 174°–175°C.

The following compounds are typical of those prepared using the method of the foregoing example: m-propionamido trifluoroacetanilide, m-propionamido butyranilide, m-isobutyramido trifluoroacetanilide and m-isobutyramido butyranilide.

EXAMPLE 4

Preparation of Meta-propionamido cyclopropane carboxanilide

Meta-aminopropionanilide, 13.1g. (0.08 mole) is dissolved in 200 ml. of a 50/50 v/v mixture of glacial acetic acid and saturated sodium acetate solution. To this solution is added 9.2g. (0.088 moles) of cyclopropane carbonyl chloride. The chloride is added slowly with adequate stirring and cooling. The product, which crystallizes from the solution, is collected by filtration. The product is consecutively washed with a 5 percent solution of sodium hydroxide, a 5 percent solution of hydrochloric acid and water. After washing, the crystals are dried. There is obtained 15g. (81 percent of theory) of the title compound, m.p. 185°–186°C.

The following compounds are typical of those prepared using the method of the foregoing example: m-propionamido cyclohexanecarboxanilide, m-propionamido phenyl-acetanilide, m-propionamido crotonanilide, and m-propionamido furoanilide.

EXAMPLE 5

Preparation of Meta-propionamido-3,3-dimethyl butylanilide

Meta-aminopropionanilide, 180g. (1.1 moles) is dissolved in 500 ml. of acetone containing 126g. of triethylamine. To this solution is added 164g. (1.22 moles) of 3,3-dimethyl butyryl chloride. The chloride is added slowly and the reaction mixture is adequately stirred and cooled, with an ice bath. The mixture is poured into water and consecutively washed with 5 percent hydrochloric acid solution, 5 percent sodium hydroxide solution, and water. After washing, the material is dried. There is obtained 178g. (62 percent of theory) of the title compound, m.p. 179.5°–181.5°C.

The following compounds are typical of those prepared using the method of the foregoing example: m-propionamido-2,2-dimethyl valeranilide, m-propionamido-2 ethyl butyranilide, m-propionamido pivalanilide, and m-pivalamino-2-2-dimethyl valeranilide.

The following is a table of the compounds which are prepared according to the aforedescribed procedures. Compound numbers have been assigned to them and are used for identification throughout the balance of the specification.

Table I

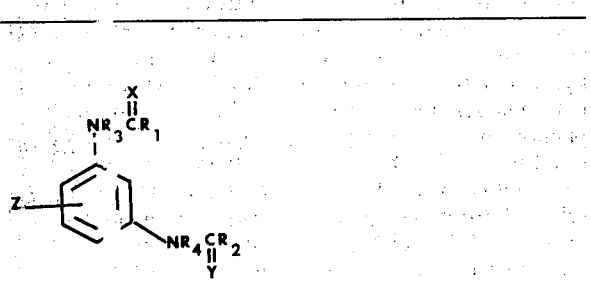

| Compound Number | X | Y | R₁ | R₂ | R₃ | R₄ | Z | m.p. °C |
|---|---|---|---|---|---|---|---|---|
| 1 | O | O | C₂H₅ | C₂H₅ | H | H | | 174–175 |
| 2 | O | O | furyl | furyl | H | H | | 191–194 |
| 3 | O | O | CH₃ | CH₃ | H | H | | 186–188 |
| 4 | O | O | CH₃ | C₂H₅ | H | H | | 239–243 |
| 5 | O | O | CH₃ | i-C₃H₇ | H | H | | 165–167 |
| 6 | O | O | n-C₃H₇ | n-C₃H₇ | H | H | | 142.5–143 |
| 7 | O | O | i-C₃H₇ | i-C₃H₇ | H | H | | 205–206 |
| 8 | O | O | C₂H₅ | CCl₃ | H | H | | 159–161 |
| 9 | O | O | H | H | H | H | | 152–154 |
| 10 | O | O | C₂H₅ | CH₂Cl | H | H | | 164–167 |
| 11 | O | O | C₂H₅ | CF₃ | H | H | | 196–197 |
| 12 | O | O | C₂H₅ | C₃H₇ | H | H | | 156–157 |

Table I-continued

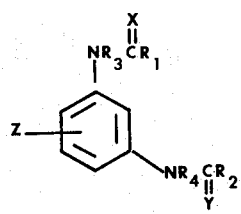

| Compound Number | X | Y | R₁ | R₂ | R₃ | R₄ | Z | m.p. °C. |
|---|---|---|---|---|---|---|---|---|
| 13 | O | O | $C_2H_5$ | $i\text{-}C_3H_7$ | H | H | | 174–175.5 |
| 14 | O | O | $C_2H_5$ | cyclopropyl | H | H | | 186–188 |
| 15 | O | O | $C_2H_5$ | $i\text{-}C_4H_9$ | H | H | | 130–131 |
| 16 | O | O | $C_2H_5$ | $n\text{-}C_5H_{11}$ | H | H | | 173–178 |
| 17 | O | O | $CH_2Cl$ | $CH_2Cl$ | H | H | | 211–212 |
| 18 | O | O | $CHCl_2$ | $CHCl_2$ | H | H | | 158–160 |
| 19 | O | O | $CH_2CH_2Cl$ | $CH_2CH_2Cl$ | H | H | | 160–163 |
| 20 | O | O | $CH=CH_2$ | $CH=CH_2$ | H | H | | 167–170 |
| 21 | O | O | $CH=CHCH_3$ | $CH=CHCH_3$ | H | H | | 215–217.5 |
| 22 | O | O | cyclopropyl | cyclopropyl | H | H | | 217–221 |
| 23 | O | O | $i\text{-}C_4H_9$ | $i\text{-}C_4H_9$ | H | H | | 226–230 |
| 24 | O | O | $n\text{-}C_5H_{11}$ | $n\text{-}C_5H_{11}$ | H | H | | 122–125 |
| 25 | O | O | $n\text{-}C_6H_{13}$ | $n\text{-}C_6H_{13}$ | H | H | | 109–113 |
| 26 | O | O | cyclohexyl | cyclohexyl | H | H | | 210–212.5 |
| 27 | O | O | benzyl | benzyl | H | H | | 194–197 |
| 28 | O | O | $CCl_3$ | $CCl_3$ | H | H | | 204–207 |
| 29 | O | O | $C(CH_3)_2Br$ | $C(CH_3)_2Br$ | H | H | | 126–128 |
| 30 | O | O | $t\text{-}C_4H_9$ | $t\text{-}C_4H_9$ | H | H | | 188–189 |
| 31 | O | O | $CH(C_2H_5)_2$ | $CH(C_2H_5)_2$ | H | H | | 148–151 |
| 32 | O | O | phenyl | phenyl | H | H | | 234–237.5 |
| 33 | O | O | $3\text{-}NO_2\text{—phenyl}$ | $3\text{-}NO_2\text{—phenyl}$ | H | H | | 250–255 |
| 34 | O | O | $C_2H_5$ | $CHCl_2$ | H | H | | 159–163 |
| 35 | O | O | $CH=CH_2$ | $C_2H_5$ | H | H | | 165–166.5 |
| 36 | O | O | $C_2H_5$ | $CH_2CH_2Cl$ | H | H | | 139–142 |
| 37 | O | O | $C_2H_5$ | $CH=CHCH_3$ | H | H | | 183–186 |
| 38 | O | O | $C_2H_5$ | $C(CH_3)_2Br$ | H | H | | 165–167 |
| 39 | O | O | $C_2H_5$ | $n\text{-}C_6H_{13}$ | H | H | | 256–260 |
| 40 | O | O | $C_2H_5$ | furyl | H | H | | 151–152.5 |
| 41 | O | O | $C_2H_5$ | cyclohexyl | H | H | | 300–304 |
| 42 | O | O | $C_2H_5$ | phenyl | H | H | | 210–213 |
| 43 | O | O | $C_2H_5$ | $3\text{-}NO_2\text{—phenyl}$ | H | H | | 198–201 |
| 44 | O | O | $C_2H_5$ | benzyl | H | H | | 129–130 |
| 45 | O | O | $i\text{-}C_3H_7$ | cyclopropyl | H | H | | 184–187 |
| 46 | O | O | $i\text{-}C_3H_7$ | $CH=CH_2$ | H | H | | 186–190 |
| 47 | O | O | $i\text{-}C_3H_7$ | $n\text{-}C_4H_9$ | H | H | | 124–126 |
| 48 | O | O | $i\text{-}C_3H_7$ | $i\text{-}C_4H_9$ | H | H | | 141–143 |
| 49 | O | O | $i\text{-}C_3H_7$ | furyl | H | H | | 152–154 |
| 50 | O | O | $i\text{-}C_3H_7$ | cyclohexyl | H | H | | 142–145 |
| 51 | O | O | $i\text{-}C_3H_7$ | phenyl | H | H | | 152–153 |
| 52 | O | O | $i\text{-}C_3H_7$ | $3\text{-}NO_2\text{—phenyl}$ | H | H | | 156–161 |
| 53 | O | O | $CHClCH_3$ | $CHClCH_3$ | H | H | | 169.5–173 |
| 54 | O | O | $C(CH_3)=CH_2$ | $C(CH_3)=CH_2$ | H | H | | 139–141 |
| 55 | O | O | $C(CH_3)_2C_3H_7$ | $C(CH_3)_2C_3H_7$ | H | H | | 96–100 |
| 56 | O | O | $CHClCH_3$ | $C_2H_5$ | H | H | | 164–166 |
| 57 | O | O | $C_2H_5$ | $C(CH_3)=CH_2$ | H | H | | 154–157 |
| 58 | O | O | $i\text{-}C_3H_7$ | $CH_2Cl$ | H | H | | 205–209 |
| 59 | O | O | $i\text{-}C_3H_7$ | $CHCl_2$ | H | H | | 178–180.5 |
| 60 | O | O | $i\text{-}C_3H_7$ | $CCl_3$ | H | H | | 160–162 |
| 61 | O | O | $i\text{-}C_3H_7$ | $CHClCH_3$ | H | H | | 168–172 |
| 62 | O | O | $i\text{-}C_3H_7$ | $CH_2CH_2Cl$ | H | H | | 179–183 |
| 63 | O | O | $i\text{-}C_3H_7$ | $CH=CHCH_3$ | H | H | | 157–160 |
| 64 | O | O | $i\text{-}C_3H_7$ | $C(CH_3)=CH_2$ | H | H | | 156–159 |
| 65 | O | O | $i\text{-}C_3H_7$ | $n\text{-}C_3H_7$ | H | H | | 146–148.5 |
| 66 | O | O | $i\text{-}C_3H_7$ | $C(CH_3)_2Br$ | H | H | | 151–153 |
| 67 | O | O | $i\text{-}C_3H_7$ | $n\text{-}C_5H_{11}$ | H | H | | 122–126 |
| 68 | O | O | $i\text{-}C_3H_7$ | $CH(C_2H_5)_2$ | H | H | | 157–158 |
| 69 | O | O | $i\text{-}C_3H_7$ | $n\text{-}C_6H_{13}$ | H | H | | 114–116 |
| 70 | O | O | $i\text{-}C_3H_7$ | benzyl | H | H | | 164–167 |
| 71 | O | O | $CF_3$ | $CF_3$ | H | H | | 207–211 |
| 72 | O | O | $CH_2C(CH_3)_3$ | $C_2H_5$ | H | H | | 177–179 |
| 73 | O | O | $2,4\text{-}diCl\text{—phenyl}$ | $C_2H_5$ | H | H | | 210–212 |
| 74 | O | O | $3,4\text{-}diCl\text{—phenyl}$ | $C_2H_5$ | H | H | | 175–177 |
| 75 | O | O | $4\text{-}NO_2\text{—phenyl}$ | $C_2H_5$ | H | H | | 227–230 |
| 76 | O | O | $CH_2C(CH_3)_3$ | $i\text{-}C_3H_7$ | H | H | | 151–153 |
| 77 | O | O | $2,4\text{-}diCl\text{—phenyl}$ | $i\text{-}C_3H_7$ | H | H | | 186–188 |
| 78 | O | O | $3,4\text{-}diCl\text{—phenyl}$ | $i\text{-}C_3H_7$ | H | H | | 189–191 |
| 79 | O | O | $C(CH_3)_2C_3H_7$ | $C_2H_5$ | H | H | | 112–115 |
| 80 | O | O | $CH(C_2H_5)$ | $C_2H_5$ | H | H | | 153–157 |
| 81 | O | O | $t\text{-}C_4H_9$ | $C_2H_5$ | H | H | | 177–179 |
| 82 | O | O | $CCl_3$ | $t\text{-}C_4H_9$ | H | H | | 169–173 |
| 83 | O | O | $C(CH_3)_2C_3H_7$ | $t\text{-}C_4H_9$ | H | H | | 119–120 |
| 84 | O | O | $CF_3$ | $t\text{-}C_4H_9$ | H | H | | >300 |
| 85 | O | O | $C(CH_3)_2C_6H_{13}$ | $t\text{-}C_4H_9$ | H | H | | 95–101 |

Table I-continued

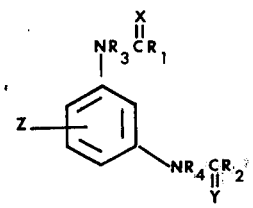

| Compound Number | X | Y | R₁ | R₂ | R₃ | R₄ | Z | m.p. °C. |
|---|---|---|---|---|---|---|---|---|
| 86 | O | O | C(CH₃)₂C₆H₁₃ | C(CH₃)₂C₆H₁₃ | H | H | | 94–98 |
| 87 | O | O | CCl₂CH₃ | CCl₂CH₃ | H | H | | 135.5–137.5 |
| 88 | O | O | CCl₂CH₃ | C₂H₅ | H | H | | 163–165 |
| 89 | O | O | CH₂C(CH₃)₃ | CH₂C(CH₃)₃ | H | H | | 187–190.5 |
| 90 | O | O | CCl₃ | CH₂C(CH₃)₃ | H | H | | 176–180 |
| 91 | O | O | CCl₃ | CH₂C(CH₃)₃ | H | H | | 177–180 |
| 92 | O | O | CF₃ | CH₂C(CH₃)₃ | H | H | | 200–201 |
| 93 | O | O | CCl₂CH₃ | CH₂C(CH₃)₃ | H | H | | 155.5–159 |
| 94 | O | O | C(CH₃)₃ | CH₂C(CH₃)₃ | H | H | | 184–185 |
| 95 | O | O | C(CH₃)₂C₃H₇ | CH₂C(CH₃)₃ | H | H | | 105–110 |
| 96 | O | O | C(CH₃)₃ | C₃H₇ | H | H | | 133–134 |
| 97 | O | O | CF₃ | C(CH₃)₂C₃H₇ | H | H | | 117–120 |
| 98 | O | O | CCl₃ | C(CH₃)₂C₃H₇ | H | H | | 119–122 |
| 99 | O | O | C(CH₃)₂Br | C₂H₅ | H | H | | 144–147 |
| 100 | O | O | CH=C(CH₃)₂ | C₂H₅ | H | H | | 66–72 |
| 101 | O | O | CH—C₂H₅ )₂ | C₂H₅ | H | H | | 155.5–156 |
| 102 | O | O | CH₂CH₂CH(CH₃)₂ | C₂H₅ | H | H | | 127–130 |
| 103 | O | O | CH₂OCH₃ | CH₂C(CH₃)₃ | H | H | | $n_D^{30}$=1.5441 |
| 104 | O | O | CH=C(CH₃)₂ | CH=C(CH₃)₂ | H | H | | (glass) |
| 105 | O | O | CH=C(CH₃)₂ | C(CH₃)₃ | H | H | | 112–117 |
| 106 | O | O | CH₂CH₂CH(CH₃)₂ | C(CH₃)₃ | H | H | | 109–112 |
| 107 | O | O | CH=C(CH₃)₂ | C(CH₃)₂C₃H₇ | H | H | | (glass) |
| 108 | O | O | CH₂CH(CH₃)CH₂C(CH₃)₃ | C₂H₅ | H | H | | 108–111 |
| 109 | O | O | CH₂CH(CH₃)₂ | CH₂CH(CH₃)₂ | H | H | | 150–152 |
| 110 | O | O | CH₂CH₂CH(CH₃)₂ | C(CH₃)₂H₇ | H | H | | 114–116 |
| 111 | O | O | CH₂CH(CH₃)CH₂C(CH₃)₃ | C(CH₃)₃ | H | H | | 48–51 |
| 112 | O | O | CH₂CH(CH₃)CH₂C(CH₃)₃ | C(CH₃)₂C₃H₇ | H | H | | (glass) |
| 113 | O | O | CH(CH₃)C₂H₅ | C₂H₅ | H | H | | 150–151 |
| 114 | O | O | CH(CH₃)C₂H₅ | CH(CH₃)C₂H₅ | H | H | | 159–161 |
| 115 | O | O | CH(CH₃)C₂H₅ | C(CH₃)₃ | H | H | | 169–171 |
| 116 | O | O | CH₂C(CH₃)₃ | CH(CH₃)C₂H₅ | H | H | | 146–149 |
| 117 | O | O | CF₃ | CH(CH₃)C₂H₅ | H | H | | 157–158 |
| 118 | O | O | 2-Cl—phenyl | C₂H₅ | H | H | | 143.5–144.5 |
| 119 | O | O | 4-Cl—phenyl | C₂H₅ | H | H | | 223–224.5 |
| 120 | O | O | 2-CH₃O—phenyl | C₂H₅ | H | H | | 124–125 |
| 121 | O | O | 4-CH₃O—phenyl | C₂H₅ | H | H | | 223–224 |
| 122 | O | O | 4-CH₃—phenyl | C₂H₅ | H | H | | 211–212 |
| 123 | O | O | 4-Cl—phenyl | C(CH₃)₃ | H | H | | 191–195 |
| 124 | O | O | benzyl | C(CH₃)₃ | H | H | | 164–165 |
| 125 | O | O | benzyl | CH(CH₃)C₂H₅ | H | H | | 161–163 |
| 126 | O | O | benzyl | CH(CH₃)C₃H₇ | H | H | | 149.5–151 |
| 127 | O | O | benzyl | C(CH₃)₂C₃H₇ | H | H | | 142–143.5 |
| 128 | O | O | styryl | C₂H₅ | H | H | | 160–163 |
| 129 | O | O | —CH₂CH₃ | CH(CH₃)₂ | H | H | 4'-Cl | 161–162 |
| 130 | O | O | C(CH₃)₃ | CH(CH₃)₂ | H | H | 4'-Cl | 176.5–178.5 |
| 131 | O | O | CH₂C(CH₃)₃ | CH(CH₃)₂ | H | H | 4'-Cl | 194–194.5 |
| 132 | O | O | CCl₃ | CH(CH₃)₂ | H | H | 4'-Cl | 156–158 |
| 133 | O | O | benzyl | CH(CH₃)₂ | H | H | 4'-Cl | 211–212 |
| 134 | O | O | C₂H₅ | C₂H₅ | C₂H₅ | H | | 132–133 |
| 135 | O | O | CH₂C(CH₃)₃ | C₂H₅ | C₂H₅ | H | | 178.5–180 |
| 136 | O | O | CH₂OCH₃ | C(CH₃)₃ | H | H | | 108–109 |
| 137 | O | O | CH₂CH₂CH(CH₃)₂ | C(CH₃)₃ | H | H | | 115–116 |
| 138 | O | O | CH₂CH₂CH(CH₃)₂ | CH₂CH₂CH(CH₃)₂ | H | H | | 151–153 |
| 139 | O | O | CH₂CH₂CH(CH₃)₂ | C(CH₃)₂C₃H₇ | H | H | | 121–123 |
| 140 | O | O | CH₂CH₂—phenyl | CH₂C(CH₃)₃ | H | H | | 101–107 |
| 141 | O | O | C₂H₅ | C₂H₅C(CH₃)₃ | H | H | | 178–179 |
| 142 | O | O | CH₂CH₂C(CH₃)₃ | CH(CH₃)C₃H₇ | H | H | | 75–77 |
| 143 | O | O | CH₂CH₂C(CH₃)₃ | CH₂C(CH₃)₃ | H | H | | 184–185 |
| 144 | O | O | CH₂CH₂C(CH₃)₃ | CH₂CH₂C(CH₃)₃ | H | H | | 216–218 |
| 145 | O | O | CH₂CH₂C(CH₃)₃ | C(CH₃)₂C₃H₇ | H | H | | 151–153 |
| 146 | O | O | C(CH₃)₂CH₂Cl | C(CH₃)₂CH₂Cl | H | H | | 145–150 |
| 147 | O | O | C(CH₃)₂CH₂Cl | C₂H₅ | H | H | | 161–164 |
| 148 | O | O | C(CH₃)₂CH₂Cl | C(CH₃)₂C₃H₇ | H | H | | 110–112 |
| 149 | O | O | C₂H₅ | CH₂O-2,4diCl—phenyl | H | H | | 206–207 |
| 150 | O | O | CH₂CH=CH₂ | C₂H₅ | H | H | | 135–139 |
| 151 | O | O | CH₂CH=CH₂ | CH₂CH=CH₂ | H | H | | 99–108 |
| 152 | O | O | C(CH₃)=CH₂ | C(CH₃)₃ | H | H | | 159–166 |
| 153 | O | O | cyclopropyl | C(CH₃)₃ | H | H | | 176–178 |
| 154 | O | O | CH(CH₃)C₃H₇ | C₂H₅ | H | H | | 147–149 |
| 155 | O | O | CH(CH₃ )C₂H₅ | C₂H₅ | H | H | | 141–144 |
| 156 | O | O | C₃H₇-n | C(CH₃)₃ | H | H | | 172–175 |
| 157 | O | O | CH₂CH(CH₃)₂ | C(CH₃)₃ | H | H | | 164.5–167 |
| 158 | O | O | n-C₄H₉ | C(CH₃)₃ | H | H | | 125–127 |

Table I-continued

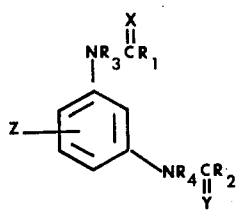

| Compound Number | X | Y | R₁ | R₂ | R₃ | R₄ | Z | m.p. °C. |
|---|---|---|---|---|---|---|---|---|
| 159 | O | O | C(CH₃)₂CH₂Cl | C(CH₃)₃ | H | H | | 151–153 |
| 160 | O | O | CH₂CH₂cyclopentyl | C₂H₅ | H | H | | 165–166 |
| 161 | O | O | CH(C₂H₅)₂ | C(CH₃)₃ | H | H | | 168–170 |
| 162 | O | O | CH(CH₃)C₃H₇ | C(CH₃)₃ | H | H | | 145–148 |
| 163 | O | O | CH(CH₃)₂ | C(CH₃)₂C₃H₇ | H | H | | 115–120 |
| 164 | O | O | CH₂CH₂cyclohexyl | C₂H₅ | H | H | | 154–155 |
| 165 | O | O | cyclohexyl | C(CH₃)₃ | H | H | | 187–188 |
| 166 | O | O | CH(CH₃)C₃H₇ | CH(CH₃)C₃H₇ | H | H | | 111–115 |
| 167 | O | O | C(CH₃)₂C₂H₅ | C(CH₃)₂C₂H₅ | H | H | | 156–158 |
| 168 | O | O | pinonoyl | C₂H₅ | H | H | | glass |
| 169 | O | O | C(CH₃)₂C₂H₅ | C(CH₃)₂C₃H₇ | H | H | | 120.5–123 |
| 170 | O | O | CH(CH₃)C₃H₇ | C(CH₃)₂C₃H₇ | H | H | | glass |
| 171 | O | O | cyclohexyl | cyclohexyl | H | H | | 217–219 |
| 172 | O | O | cyclohexyl | C(CH₃)₂C₃H₇ | H | H | | 153.5–157 |
| 173 | O | O | 3-4-diCl—phenyl | C(CH₃)₃ | H | H | | 187–191 |
| 174 | O | O | CH₃O-2,4-diCl—phenyl | C(CH₃)₃ | H | H | | 163–165 |
| 175 | O | O | 3,4-diCl—phenyl | C(CH₃)C₃H₇ | H | H | | 107–114 |
| 176 | O | O | 2,4-diCl—phenyl | C(CH₃)₂C₃H₇ | H | H | | 153–157 |
| 177 | O | O | CH₃O-2,4-diCl—phenyl | C(CH₃)C₃H₇ | H | H | | 126–129 |
| 178 | O | O | C(i-C₃H₇)₂CH₃ | C₂H₅ | H | H | | $n_D^{30}$ 1.5225 |
| 179 | O | O | CH=CHCH₃ | C(CH₃)₃ | H | H | | 67–69 |
| 180 | O | O | CH₃CH=CH₂ | C(CH₃)₃ | H | H | | 159–161 |
| 181 | O | O | CH₂CH₂cyclopentyl | C(CH₃)₃ | H | H | | 142–143 |
| 182 | O | O | CH₂CH₂cyclohexyl | C(CH₃)₃ | H | H | | 141.5–143 |
| 183 | O | O | 3′-pinonyl | C(CH₃)₃ | H | H | | 61–67 |
| 184 | O | O | 2,4-diCl—phenyl | C(CH₃)₃ | H | H | | 182–184 |
| 185 | O | O | C(i-C₃H₇)₂CH₃ | C(CH₃)₃ | H | H | | 62–66 |
| 186 | O | O | CCl₃ | CH(CH₃)C₃H₇ | H | H | | 121–126 |
| 187 | O | O | CF₃ | CH(CH₃)C₃H₇ | H | H | | 139–146 |
| 188 | O | O | CH(CH₃)₂ | CH(CH₃)C₃H₇ | H | H | | 156–157 |
| 189 | O | O | CH(CH₃)C₂H₅ | CH(CH₃)C₃H₇ | H | H | | 145–147 |
| 190 | O | O | C(CH₃)₂CH₂Cl | CH(CH₃)C₃H₇ | H | H | | $n_D^{30}$ 1.5145 |
| 191 | O | O | CH₂C(CH₃)₃ | CH(CH₃)C₃H₇ | H | H | | $n_D^{30}$ 1.5078 |
| 192 | O | O | CH₂CH(CH₃)CH₂C(CH₃)₃ | CH(CH₃)C₃H₇ | H | H | | $n_D^{30}$ 1.5020 |
| 193 | O | O | CH₂O-2,4-diCl—phenyl | CH(CH₃)C₃H₇ | H | H | | 182.184 |
| 194 | O | O | C(CH₃)₃ | C(C₂H₅)₂CH₃ | H | H | | 131–134.5 |
| 195 | O | O | CH₂C(CH₃)₃ | C(C₂H₅)₂CH₃ | H | H | | 133–135 |
| 196 | O | O | CH₂CH(CH₃)CH₂C(CH₃)₃ | C(C₂H₅)₂CH₃ | H | H | | 57–62 |
| 197 | O | O | CH₂CH(CH₃)C₂H₅ | C₂H₅ | H | H | | 123–126 |
| 198 | O | O | CH₂CH(CH₃)C₂H₅ | C(CH₃)₃ | H | H | | 134–136 |
| 199 | O | O | CH₂CH(CH₃)C₂H₅ | CH(CH₃)C₃H₇ | H | H | | 107–108 |
| 200 | O | O | CH₂CH(CH₃)C₂H₅ | C(CH₃)₂C₃H₇ | H | H | | 100–103 |
| 201 | O | O | CH₂CH(CH₃)C₂H₅ | CH₂CH(CH₃)C₂H₅ | H | H | | 132–134 |
| 202 | O | O | CH(C₂H₅)C₄H₉ | C₂H₅ | H | H | | 126–129 |
| 203 | O | O | CH(C₂H₅)C₄H₉ | CH(C₂H₅)C₄H₉ | H | H | | 53–70 |
| 204 | O | O | CH₂C(CH₃)₃ | CH(CH₃)CH₃ | H | H | | 189–192 |
| 205 | O | O | C₂H₅ | C(C₂H₅)₂CH₃ | H | H | | 134–137 |
| 206 | O | O | CH(CH₃)C₃H₇ | C(C₂H₅)₂CH₃ | H | H | | 45–48 |
| 207 | O | O | CH₂C(CH₃)₂C₂H₅ | C₂H₅ | H | H | | 174–175 |
| 208 | O | O | CH₂C(CH₃)₂C₂H₅ | C(CH₃)₃ | H | H | | 156–157 |
| 209 | O | O | CH(C₂H₅)C₄H₉ | C(CH₃)₃ | H | H | | 132–134 |
| 210 | O | O | CH(C₂H₅)C₃H₇ | CH(CH₃C₃H₇ | H | H | | 108–112 |
| 211 | O | O | CH(C₂H₅)C₄H₉ | C(C₂H₅)₂C₃H₇ | H | H | | 119–121 |
| 212 | O | O | CH₂C(CH₃)₂C₂H₅ | CH(CH₃)C₃H₇ | H | H | | 135–136 |
| 213 | O | O | CH₂C(CH₃)₂C₂H₅ | C(CH₃)C₃H₇ | H | H | | 108–110 |
| 214 | O | O | CH₂C(CH₃)₂C₂H₅ | CH₂C(CH₃)₂C₂H₅ | H | H | | 175–178 |
| 215 | O | O | C₂F₅ | C₂H₅ | H | H | | 172–175 |
| 216 | O | O | C₂F₅ | C(CH₃)₃ | H | H | | 187–190 |
| 217 | O | O | C₂F₅ | CH(CH₃)C₃H₇ | H | H | | 126–128 |
| 218 | O | O | C₂F₅ | C(CH₃)₂C₃H₇ | H | H | | 112–114 |
| 219 | O | O | CCl₂CF₃ | C₂H₅ | H | H | | 141–143 |
| 220 | O | O | 2-CH₃—phenyl | C(CH₃)₃ | H | H | | 185–186.5 |
| 221 | O | O | 3-CH₃—phenyl | C(CH₃)₃ | H | H | | 163–164 |
| 222 | O | O | 4-CH₃—phenyl | C(CH₃)₃ | H | H | | 206–207 |
| 223 | O | O | 2-CH₃—phenyl | CH(CH₃)C₃H₇ | H | H | | 172–174 |
| 224 | O | O | 3-CH₃—phenyl | CH(CH₃)C₃H₇ | H | H | | 68–72 |
| 225 | O | O | 4-CH₃—phenyl | CH(CH₃)C₃H₇ | H | H | | 122–124 |
| 226 | O | O | 2-CH₃—phenyl | C(CH₃)₂C₃H₇ | H | H | | 154–155 |
| 227 | O | O | 3-CH₃—phenyl | C(CH₃)₂C₃H₇ | H | H | | 129–130 |
| 228 | O | O | 4-CH₃—phenyl | C(CH₃)₂C₃H₇ | H | H | | 146–148 |
| 229 | O | O | 2-Cl—phenyl | C(CH₃)₃ | H | H | | 185–187 |
| 230 | O | O | 3-Cl—phenyl | C(CH₃)₃ | H | H | | 193–194 |
| 231 | O | O | 2-Cl—phenyl | CH(CH₃)C₃H₇ | H | H | | 154–156 |

Table I-continued

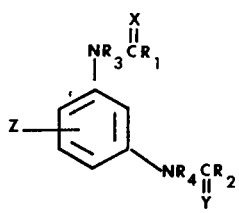

| Compound Number | X | Y | R₁ | R₂ | R₃ | R₄ | Z | m.p. °C. |
|---|---|---|---|---|---|---|---|---|
| 232 | O | O | 3-Cl—phenyl | CH(CH₃)C₃H₇ | H | H | | 118-120 |
| 233 | O | O | 4-Cl—phenyl | CH(CH₃)C₃H₇ | H | H | | 131-133 |
| 234 | O | O | 2-Cl—phenyl | C(CH₃)₂C₃H₇ | H | H | | 128-130 |
| 235 | O | O | 3-Cl—phenyl | C(CH₃)₂C₃H₇ | H | H | | 132-133 |
| 236 | O | O | 4-Cl—phenyl | C(CH₃)₂C₃H₇ | H | H | | 135-137 |
| 237 | O | O | 2-F—phenyl | C₂H₅ | H | H | | 186-187 |
| 238 | O | O | 4-F—phenyl | C₂H₅ | H | H | | 205-206 |
| 239 | O | O | 2-F—phenyl | C(CH₃)₃ | H | H | | 123-126 |
| 240 | O | O | 4-F—phenyl | C(CH₃)₃ | H | H | | 195-196 |
| 241 | O | O | 2-F—phenyl | CH(CH₃)C₃H₇ | H | H | | 129-131 |
| 242 | O | O | 4-F—phenyl | CH(CH₃)C₃H₇ | H | H | | 141-143 |
| 243 | O | O | 2-F—phenyl | C(CH₃)₂C₃H₇ | H | H | | 114-115 |
| 244 | O | O | 4-F—phenyl | C(CH₃)₂C₃H₇ | H | H | | 147-149 |
| 245 | O | O | CH(C₂H₅)₂ | CH(CH₃)C₃H₇ | H | H | | 157-159 |
| 246 | O | O | CH(CH₃)C₃H₇ | CH(CH₃)C₃H₇ | H | H | 3-Cl | 63-66 |
| 247 | O | O | C₂H₅ | C₂H₅ | H | H | 2-CH₃ | 266-267 |
| 248 | O | O | i-C₃H₇ | i-C₃H₇ | H | H | 2-CH₃ | 295-296 |
| 249 | O | O | t-C₄H₉ | t-C₄H₉ | H | H | 2-CH₃ | 260-261 |
| 250 | O | O | CH(CH₃)C₃H₇ | CH(CH₃)C₃H₇ | H | H | 2-CH₃ | 245-246 |
| 251 | O | O | C(CH₃)₂C₃H₇ | C(CH₃)₂C₃H₇ | H | H | 2-CH₃ | 176-177 |

Other examples of compounds falling within the generic formulas presented herein, which are preparable by the above-described procedures and which may be formulated into herbicidal compositions and applied as herein illustrated are:

| X | Y | R₁ | R₂ | R₃ | R₄ | Z |
|---|---|---|---|---|---|---|
| O | S | H | H | H | H | |
| O | S | C₂H₅ | H | H | H | |
| O | S | C₂H₅ | C₂H₅ | H | H | |
| O | S | C₂H₅ | cyclopropyl | H | H | |
| O | S | CH₂Cl | CH₂Cl | H | H | |
| O | S | cyclopropyl | n-C₅H₁₁ | H | H | |
| O | S | CH=CHCH₃ | C₂H₅ | H | H | |
| O | S | furyl | furyl | H | H | |
| O | S | CCl₃ | C₂H₅ | H | H | |
| O | S | phenyl | phenyl | H | H | |
| O | S | cyclohexyl | cyclohexyl | H | H | |
| O | S | benzyl | C₂H₅ | H | H | |
| O | S | 2,4-diCl-phenyl | C₂H₅ | H | H | |
| O | S | 4-NO₂-phenyl | C₂H₅ | H | H | |
| O | S | 3,4-diCl-phenyl | i-C₃H₇ | H | H | |
| O | S | C₂H₅ | CF₃ | H | H | |
| O | S | t-C₄H₉ | t-C₄H₉ | H | H | |
| O | S | phenyl | phenyl | H | H | |
| O | S | cyclohexyl | cyclohexyl | H | H | 5'-Cl |
| O | S | C₂H₅ | 3-NO₂—phenyl | H | H | 5'-Cl |
| O | O | C₂H₅ | i-C₃H₇ | H | H | 5'-Br |
| O | O | C₂H₅ | i-C₃H₇ | H | H | 5'-F |
| O | O | C₂H₅ | i-C₃H₇ | H | H | 5'-C₂H₅ |
| O | O | C₂H₅ | i-C₃H₇ | H | H | 5'-NO₂ |
| O | O | C₂H₅ | i-C₃H₇ | H | H | 5'-CF₃ |
| O | O | C₂H₅ | i-C₃H₇ | H | CH₃ | |
| O | S | C₂H₅ | CH(C₂H₅)2 | H | CH₃ | 5'-Cl |
| O | S | C₂H₅ | phenyl | H | CH₃ | 5'-NO₂ |
| O | O | CH₂C(CH₃)₃ | C₂H₅ | CH₃ | CH₃ | |
| O | O | CH₂C(CH₃)₃ | C₂H₅ | CH₃ | H | 5'-Cl |
| O | O | C₂H₅ | i-C₃H₇ | CH₃ | H | 5'-CF₃ |
| O | O | C(CH₃)₂C₃H₇ | C₂H₅ | C₂H₅ | CH₃ | 5'-NO₂ |
| O | S | C₂H₅ | i-C₃H₇ | CH₃ | CH₃ | 5'-CH₃ |
| O | O | H | H | H | H | 5'-NH₂ |
| O | O | C₂H₅ | C₂H₅ | H | H | 5'NH₂ |
| O | O | C₂H₅ | i-C₃H₇ | CH₃ | CH₃ | 5'-NH₂ |
| O | S | H | H | CH₃ | CH₃ | 5'-OCH₃ |
| O | S | C₂H₅ | C₂H₅ | H | H | 5'-OC₂H₅ |
| S | O | C₂H₅ | i-C₃H₇ | CH₃ | CH₃ | 5'-OCH₃ |
| S | O | C₂H₅ | i-C₃H₇ | H | CH₃ | 5'-NH₂ |
| S | O | CH₃ | i-C₃H₇ | H | H | 5'-OCH₃ |

| X | Y | R₁ | R₂ | R₃ | R₄ | Z |
|---|---|---|---|---|---|---|
| S | S | C₂H₅ | C₂H₅ | CH₃ | CH₃ | 5'-OCH₃ |
| S | S | C₂H₅ | C₂H₅ | H | H | 5'-NH₂ |
| O | O | CH₂OC₂H₅ | C₂H₅ | H | H | |
| O | O | C₂H₄OC₂H₅ | i-C₃H₇ | CH₃ | H | |

Pre-emergence herbicide test. On the day preceding treatment, seeds of seven different weed species are planted in individual rows using one species per row across the width of the flat. The seeds used are hairy crabgrass (*Digitaria sanguinalis* (L.) Scop.), yellow foxtail (*Setaria glauca* (L.) Beauv.), watergrass (*Echinochloa crusgalli* (L.) Beauv.), California red oat (*Avena sativa* (L.)), redroot pigweed (*Amaranthus retroflexus* (L.), Indian Mustard (*Brassica juncea* (L.) Coss.) and curly dock (*Rumex crispus* (L.). Ample seeds are planted to give about 20 to 50 seedlings per row, after emergence, depending on the size of the plants. The flats are watered after planting. The spraying solution is prepared by dissolving 50 mg. of the test compound in 3 ml. of a solvent, such as acetone, containing 1% Tween 20 (polyoxy-ethylene sorbitan monolaurate.) The following day, each flat is sprayed at the rate of 20 pounds of the candidate compound per 80 gallons of solution per acre. An atomizer is used to spray the solution on soil surface. The flats are placed in a greenhouse at 80°F. and watered regularly. Two weeks later, the degree of weed control is determined by comparing the amount of germination and growth of each weed in the treated flats with weeds in several untreated control flats.

The rating system is as follows:

− = no significant injury (0–15 percent control)
+ = slight injury (25–35 percent control)
++ = moderate injury (55–65 percent control)
+++ = severe injury or death (85–100 percent control)

An activity index is used to represent the total activity on all seven weed species. It is the sum of the number of plus marks, so that an activity index of 21 represents complete control of all seven weeds. The results of this test are reported in Table II.

Post-emergence Herbicide Test

Seeds of five weed species including hairy crabgrass, watergrass, wild oats, Indian mustard, and curly dock and one crop pinto beans (*Phaseolus vulgaris*), are planted in flats as described above for pre-emergence screening. The flats are placed in the greenhouse at 72°–85°F. and watered daily with a sprinkler. About 10 to 14 days after planting when the primary leaves of the bean plant are almost fully expanded and the first trifoliate leaves are just starting to form, the plants are sprayed. The spray is prepared by weighing out 50 mg. of the test compound, dissolving it in 5 ml. of acetone containing 1 percent Tween 20 (polyoxy-ethylene sorbitan monolaurate) and then adding 5 ml. of water. The solution is sprayed on the foliage using an atomizer. The spray concentration is 0.5% and the rate would be approximately 20 lb/acre if all of the spray were retained on the plant and the soil, but some spray is lost so it is estimated that the application rate is approximately 12.5 lb/acre.

Beans are used to detect defoliants and plant growth regulators. The beans are trimmed to two or three plants per flat by cutting off the excess weaker plants several days before treatment. The treated plants are placed back in the greenhouse and care is taken to avoid sprinkling the treated foliage with water for three days after treatment. Water is applied to the soil by means of a slow stream from a watering hose taking care not to wet the foliage.

Injury rates are recorded 14 days after treatment. The rating system is the same as described above for the pre-emergence test where (−), (+), (++), and (+++) are used for the different rates of injury and control. The injury symptoms are also recorded. The maximum activity index for complete control of all the species in the post-emergence screening test is 18 which represents the sum of the plus marks obtained with the six plant species used in the test. The herbicide activity index is shown in Table II.

TABLE II

HERBICIDAL ACTIVITY ** - SCREENING RESULTS

| Compound Number | Pre-emergence | Post-emergence |
|---|---|---|
| 1 | 12 | 15 |
| 2 | 2 | 12 |
| 3 | 7 | 3 |
| 4 | 1 | 0 |
| 5 | 0 | 5 |
| 6 | 9 | 5 |
| 7 | 18 | 15 |
| 8 | 15 | 18 |
| 9 | 0 | 7 |
| 10 | 0 | 8 |
| 11 | 19 | 18 |
| 12 | 11 | 16 |
| 13 | 20 | 18 |
| 14 | 17 | 15 |
| 15 | 14 | 18 |
| 16 | 0 | 13 |
| 17 | 1 | 8 |
| 18 | 0 | 9 |
| 19 | 0 | 7 |
| 20 | 0 | 10 |
| 21 | 12 | 16 |
| 22 | 12 | 15 |
| 23 | 6 | 13 |
| 24 | 6 | 12 |
| 25 | 4 | 8 |
| 26 | 8 | 9 |
| 27 | 11 | 16 |
| 28 | 9 | 14 |
| 29 | 17 | 15 |
| 30 | 21 | 17 |
| 31 | 2 | 11 |
| 32 | 0 | 8 |
| 33 | 0 | 9 |
| 34 | 9 | 16 |
| 35 | 2 | 9 |
| 36 | 9 | 15 |
| 37 | 6 | 14 |
| 38 | 20 | 18 |
| 39 | 6 | 12 |
| 40 | 11 | 12 |
| 41 | 5 | 14 |
| 42 | 10 | 12 |
| 43 | 9 | 12 |
| 44 | 8 | 18 |
| 45 | 18 | 16 |
| 46 | 8 | 11 |
| 47 | 8 | 12 |
| 48 | 6 | 12 |
| 49 | 16 | 18 |
| 50 | 5 | 12 |
| 51 | 5 | 11 |
| 52 | 6 | 12 |
| 53 | 6 | 0 |
| 54 | 12 | 12 |

TABLE II-continued
HERBICIDAL ACTIVITY ** - SCREENING RESULTS

| Compound Number | Pre-emergence | Post-emergence |
|---|---|---|
| 55 | 21 | 18 |
| 56 | 19 | 17 |
| 57 | 6 | 8 |
| 58 | 0 | 2 |
| 59 | 10 | 9 |
| 60 | 21 | 18 |
| 61 | 15 | 16 |
| 62 | 7 | 12 |
| 63 | 16 | 16 |
| 64 | 14 | 15 |
| 65 | 3 | 10 |
| 66 | 20 | 17 |
| 67 | 8 | 8 |
| 68 | 21 | 18 |
| 69 | 0 | 11 |
| 70 | 14 | 15 |
| 71 | 10 | 11 |
| 72 | 21 | 18 |
| 73 | 11 | 12 |
| 74 | 12 | 11 |
| 76 | 20 | 18 |
| 77 | 12 | 15 |
| 78 | 3 | 11 |
| 79 | 21 | 18 |
| 80 | 18 | 18 |
| 81 | 19 | 18 |
| 82 | 17 | 16 |
| 83 | 18 | 18 |
| 84 | 7 | 12 |
| 85 | 6 | 7 |
| 86 | 0 | 2 |
| 87 | 19 | 16 |
| 88 | 21 | 18 |
| 89 | 9 | 12 |
| 90 | 0 | 3 |
| 91 | 11 | 16 |
| 92 | 4 | 10 |
| 93 | 8 | 18 |
| 94 | 20 | 18 |
| 95 | 19 | 18 |
| 96 | 18 | 18 |
| 97 | 11 | 18 |
| 98 | 6 | 14 |
| 99 | 19 | 18 |
| 100 | 13 | 18 |
| 101 | 19 | 18 |
| 102 | 6 | 15 |
| 103 | 12 | 18 |
| 104 | 19 | 18 |
| 105 | 20 | 18 |
| 106 | 14 | 17 |
| 107 | 17 | 18 |
| 108 | 11 | 18 |
| 109 | 6 | 12 |
| 110 | 12 | 17 |
| 111 | 12 | 18 |
| 112 | 9 | 14 |
| 113 | 21 | 18 |
| 114 | 19 | 18 |
| 115 | 20 | 18 |
| 116 | 21 | 18 |
| 117 | 5 | 18 |
| 118 | 11 | 17 |
| 119 | 9 | 14 |
| 120 | 5 | 14 |
| 121 | 0 | 1 |
| 122 | 0 | 12 |
| 123 | 0 | 12 |
| 124 | 17 | 18 |
| 125 | 10 | 18 |
| 126 | 9 | 18 |
| 127 | 15 | 18 |
| 128 | 3 | 17 |
| 129 | 9 | 16 |
| 130 | 7 | 9 |
| 131 | 7 | 11 |
| 132 | 16 | 15 |
| 133 | 8 | 9 |
| 134 | 6 | 14 |
| 135 | 6 | 11 |
| 136 | 12 | 13 |
| 137 | 14 | 15 |
| 138 | 2 | 13 |
| 139 | 14 | 14 |
| 140 | 0 | 7 |
| 141 | 14 | 18 |
| 142 | 12 | 16 |
| 143 | 5 | 12 |
| 144 | 0 | 2 |
| 145 | 6 | 12 |
| 146 | 3 | 4 |
| 147 | 21 | 18 |
| 148 | 21 | 17 |
| 149 | 8 | 12 |
| 150 | 10 | 17 |
| 151 | 7 | 16 |
| 152 | 15 | 17 |
| 153 | 16 | 18 |
| 154 | 18 | 18 |
| 155 | 16 | 18 |
| 156 | 17 | 19 |
| 157 | 19 | 17 |
| 158 | 11 | 16 |
| 159 | 15 | 14 |
| 160 | 3 | 11 |
| 161 | 19 | 18 |
| 162 | 21 | 18 |
| 163 | 21 | 18 |
| 164 | 0 | 8 |
| 165 | 9 | 16 |
| 166 | 18 | 18 |
| 167 | 11 | 13 |
| 168 | 9 | 15 |
| 169 | 21 | 17 |
| 170 | 20 | 18 |
| 171 | 0 | 0 |
| 172 | 0 | 14 |
| 173 | 0 | 15 |
| 174 | 17 | 15 |
| 175 | 8 | 16 |
| 176 | 9 | 14 |
| 177 | 9 | 16 |
| 178 | 9 | 18 |
| 179 | 18 | 18 |
| 180 | 19 | 18 |
| 181 | 2 | 12 |
| 182 | 0 | 9 |
| 183 | 6 | 8 |
| 184 | 14 | 12 |
| 185 | 13 | 9 |
| 186 | 14 | 15 |
| 187 | 19 | 18 |
| 188 | 21 | 16 |
| 189 | 20 | 16 |
| 190 | 21 | 18 |
| 191 | 21 | 18 |
| 192 | 9 | 12 |
| 193 | 5 | 10 |
| 194 | 18 | 11 |
| 195 | 13 | 9 |
| 196 | 1 | 4 |
| 197 | 20 | 16 |
| 198 | 21 | 16 |
| 199 | 21 | 15 |
| 200 | 21 | 16 |
| 201 | 19 | 14 |
| 202 | 21 | 18 |
| 203 | 0 | 6 |
| 204 | 10 | 11 |
| 205 | 21 | 17 |
| 206 | 21 | 15 |
| 207 | 18 | 18 |
| 208 | 17 | 15 |
| 209 | 13 | 17 |
| 210 | 13 | 18 |
| 211 | 6 | 13 |
| 212 | 16 | 14 |
| 213 | 13 | 5 |
| 214 | 0 | 4 |
| 215 | 20 | 18 |
| 216 | 16 | 18 |
| 217 | 15 | 18 |
| 218 | 16 | 18 |
| 219 | 17 | 18 |
| 220 | 4 | 11 |
| 221 | 7 | 14 |
| 222 | 0 | 4 |
| 223 | 3 | 11 |
| 224 | 8 | 12 |
| 225 | 2 | 14 |
| 226 | 7 | 14 |
| 227 | 9 | 15 |
| 228 | 0 | 10 |
| 229 | 11 | 10 |
| 230 | 6 | 10 |
| 231 | 8 | 12 |
| 232 | 8 | 12 |
| 233 | 5 | 11 |

TABLE II-continued

HERBICIDAL ACTIVITY ** - SCREENING RESULTS

| Compound Number | Pre-emergence | Post-emergence |
|---|---|---|
| 234 | 9 | 13 |
| 235 | 9 | 14 |
| 236 | 6 | 12 |
| 237 | 7 | 6 |
| 238 | 11 | 10 |
| 239 | 15 | 16 |
| 240 | 8 | 9 |
| 241 | 9 | 11 |
| 242 | 8 | 12 |
| 243 | 10 | 14 |
| 244 | 6 | 11 |
| 245 | 19 | 18 |
| 246 | 0 | 14 |
| 247 | 6 | 5 |
| 248 | 0 | 5 |
| 249 | 5 | 5 |
| 250 | 3 | 4 |
| 251 | 6 | 7 |

21 = 85–100% control of all seven plant species tested pre-emergence.

18 = 85–100% control of all six plant species tested post-emergence

The compounds of the present invention are used as pre-emergence of post-emergence herbicides and are applied in a variety of ways at various concentrations. In practice, the compounds are formulated with an inert carrier, utilizing methods well-known to those skilled in the art, thereby making them suitable for application as dusts, sprays, or drenches and the like in the form and manner required. The mixtures can be dispersed in water with the aid of a wetting agent or they can be employed in organic liquid compositions, oil and water, water in oil emulsions, with or without the addition of wetting, dispersing or emulsifying agents. The amount applied depends upon the nature of the seeds or plants to be controlled and the rate of application varies from approximately 1 to approximately 50 pounds per acre. One particularly advantageous way of applying the compound is a narrow band along a row crop straddling the row. In practice, the compounds are formulated with an inert carrier utilizing methods well known to those skilled in the art, thereby making them suitable for particular application.

The phytotoxic compositions of this invention are applied to the plants in the conventional manner. Thus, the dust and liquid compositions can be applied to the plant by the use of power-dusters, boom and hand sprayers and spray-dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are preferably distributed in the soil to a depth of at least ½-inch below the soil surface. It is not necessary that the phytotoxic compositions be admixed with the soil particles and these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example fertilizers, pesticides and the like, used as adjuvant or in combination with any of the above-described adjuvants. Other phytotoxic compounds useful in combination with the above-described compounds include for example 2,4-dichlorophenoxyacetic acids, 2,4,5-trichlorophenoxyacetic acid, 2 - methyl - 4-chlorophenoxyacetic acid and the salts, esters and amides thereof; triazine derivatives, such as 2,4-bis (3-methoxypropylamino)-6-methylthio-S-triazine; 2-chloro-4-ethylamino-6-isopropylamino-S-triazine, and 2-ethylamino-4-isopropylamino-6-methyl-mercapto-S-triazine, urea derivatives, such as 3-(3,4-dichlorophenyl)-1,1-dimethyl urea and 3-(p-chlorophenyl)-1,1-dimethyl urea and acetamides such as N,N - dially - α -chloroacetamide, N-(α-chloroacetayl)hexamethylene imine, and N,N-diethyl-a-bromacetamide and the like; benzoic acids such as 3-amino-2,5-dichlorobenzoic and; thiocarbamates, such as S-propyl dipropylthiocarbamate; S-ethyl-dipropylthiocarbamate, S-ethyl-cyclohexylethyl-thiocarbamate, S-ethyl hexahydro-1H-azepine-1-carbothioate and the like. Fertilizers useful in combination with the active ingredients include for example ammonium nitrate, urea and superphosphates. Other useful additaments include materials in which plant organisms take root and grow such as compost, manure, humus, sand and the like.

The concentration of a compound of the present invention, constituting an effective amount in the best mode of administration in the utility disclosed is readily determinable by those skilled in the art. Various changes and modifications are possible without departing from the spirit and scope of the invention described herein and will be apparent to those skilled in the art to which it pertains. It is accordingly intended that the present invention shall only be limited by the scope of the claims.

What is claimed is:

1. A compound having the formula

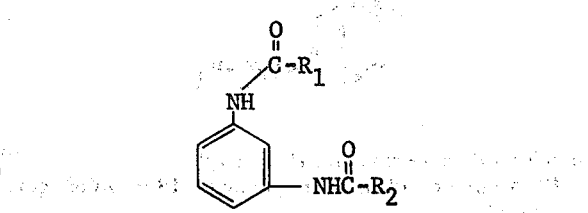

in which $R_2$ is halogenated lower alkyl, and $R_1$ is alkyl.

2. A compound according to claim 1 in which $R_1$ is ethyl and $R_2$ is 1-bromo-1-methylethyl.

3. A compound according to claim 1 in which $R_1$ is isopropyl and $R_2$ is trichloromethyl.

4. A compound according to claim 1 in which $R_1$ is isopropyl and $R_2$ is 1-chloroethyl.

5. A compound according to claim 1 in which $R_1$ is isopropyl and $R_2$ is 1-bromo-1-methylethyl.

6. A compound according to claim 1 in which $R_1$ is ethyl and $R_2$ is trifluoromethyl.

7. A compound according to claim 1 in which $R_2$ is 1-bromo-iso-propyl and $R_1$ is ethyl.

8. A compound according to claim 1 in which $R_2$ is 1,1-dichloroethyl and $R_1$ is ethyl.

9. A compound according to claim 1 in which $R_2$ is trifluoromethyl and $R_1$ is 1,1-dimethylbutyl.

10. A compound according to claim 1 in which $R_2$ is 1,1-dimethyl-2-chloroethyl and $R_1$ is ethyl.

11. A compound according to claim 1 in which $R_2$ is 1,1-dimethyl-2-chloroethyl and $R_1$ is 1,1-dimethylbutyl.

12. The compound having the formula

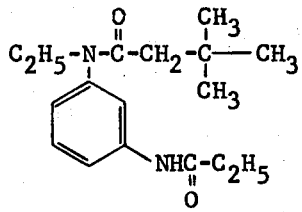

13. A compound having the formula

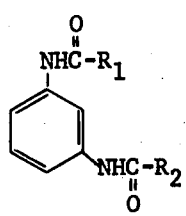

in which $R_1$ is lower alkenyl, $R_2$ is alkyl.

14. A compound according to claim 13 in which $R_1$ is 2,2-dimethylvinyl, $R_2$ is tert-butyl.

15. A compound according to claim 13 in which $R_1$ is 2,2-dimethylvinyl, $R_2$ is 1,1-dimethylbutyl.

16. A compound according to claim 13 in which $R_1$ is 2,2-dimethylvinyl, $R_2$ is ethyl.

17. A compound according to claim 13 in which $R_1$ is vinyl, $R_2$ is ethyl.

18. A compound having the formula

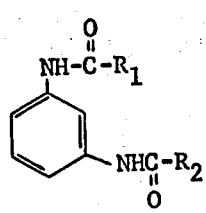

in which $R_1$ is benzyl and $R_2$ is alkyl.

19. A compound according to claim 18 in which $R_2$ is tert-butyl.

20. A compound according to claim 18 in which $R_2$ is sec-butyl.

21. A compound according to claim 18 in which $R_2$ is 1-methylbutyl.

22. A compound according to claim 18 in which $R_2$ is 1,1-dimethylbutyl.

23. A compound having the formula

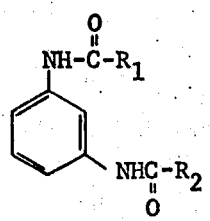

in which $R_1$ is chlorophenyl and $R_2$ is alkyl.

24. A compound according to claim 23 in which $R_1$ is 2-chlorophenyl and $R_2$ is ethyl.

25. A compound according to claim 23 in which $R_1$ is 4-chlorophenyl and $R_2$ is ethyl.

26. A compound according to claim 23 in which $R_1$ is 4-chlorophenyl and $R_2$ is tert-butyl.

27. A compound having the formula

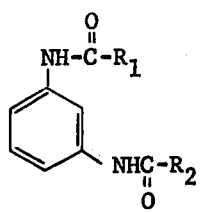

in which $R_1$ is styryl and $R_2$ is alkyl.

28. A compound according to claim 27 in which $R_2$ is ethyl.

29. A compound having the formula

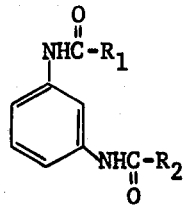

in which $R_1$ is 2,4,4-trimethylpentyl and $R_2$ is 1,1-dimethylbutyl.

30. A compound having the formula

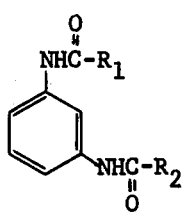

in which $R_1$ is 1,1-dimethylbutyl, $R_2$ is neopentyl.

31. A compound having the formula

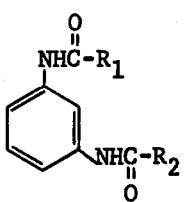

in which $R_1$ is tert.-butyl and $R_2$ is neopentyl.

32. A compound having the formula

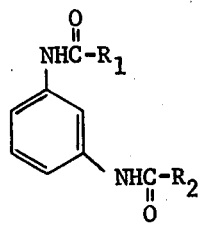

in which R₁ is 1-methylbutyl, and R₂ is tert.-butyl.

33. A compound having the formula

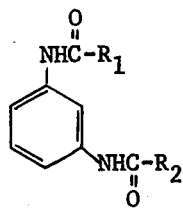

in which R₁ is 3,4-dichlorophenyl and R₂ is ethyl.

34. A compound having the formula

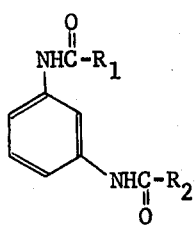

in which R₁ is 2,4-dichlorophenyl and R₂ is tert.-butyl.

35. A compound having the formula

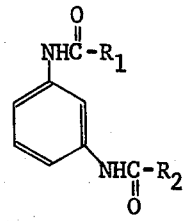

in which R₁ is cyclopropyl and R₂ is tert.-butyl.

36. Compound having the formula

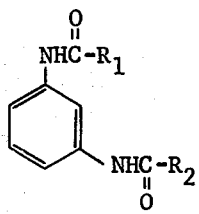

in which R₁ and R₂ are as follows:

a. R₁ is 2,2-dimethylpropyl and R₂ is isopropyl
b. R₁ is isopropyl and R₂ is 1-ethylpropyl
c. R₁ is isopropyl and R₂ is 1,1-dimethylbutyl
d. R₁ is isopropyl and R₂ is 1-methylbutyl
e. R₁ is 2-methylbutyl and R₂ is tert.-butyl
f. R₁ is 1,1-dimethylbutyl and R₂ is tert.-butyl
g. R₁ is tert.-butyl and R₂ is 2,2-dimethylpropyl
h. R₁ is 3-methylbutyl and R₂ is tert.-butyl
i. R₁ is 1-methylpropyl and R₂ is tert.-butyl
j. R₁ is 2,2-dimethylpropyl and R₂ is 1-methylpropyl
k. R₁ is 2,2-dimethylpropyl and R₂ is 1-methylbutyl
l. R₁ is 1-methylbutyl and R₂ is 1,1-dimethylbutyl
m. R₁ is 1-methylpropyl and R₂ is 1-methylbutyl
n. R₁ is 2-methylbutyl and R₂ is 1-methylbutyl
o. R₁ is 2,2-dimethylbutyl and R₂ is 1-methylbutyl
p. R₁ is 2-methylbutyl and R₂ is 1,1-dimethylbutyl.

* * * * *